US00PP26149P3

(12) United States Plant Patent
Kristensen

(10) Patent No.: US PP26,149 P3
(45) Date of Patent: Nov. 24, 2015

(54) *OSTEOSPERMUM* PLANT NAMED 'SAKOST8340'

(50) Latin Name: *Osteospermum hybrida*
Varietal Denomination: SAKOST8340

(71) Applicant: Sakata Ornamentals Europe A/S, Marslev (DK)

(72) Inventor: Niels G. Kristensen, Silkeborg (DK)

(73) Assignee: Sakata Ornamentals Europe A/S, Marslev (DK)

( * ) Notice: Subject to any disclaimer, the term of this patent is extended or adjusted under 35 U.S.C. 154(b) by 38 days.

(21) Appl. No.: 13/999,118

(22) Filed: Jan. 15, 2014

(65) Prior Publication Data

US 2015/0201540 P1 Jul. 16, 2015

(51) Int. Cl.
*A01H 5/00* (2006.01)

(52) U.S. Cl.
USPC ..... Plt./360

(58) Field of Classification Search
USPC ..... Plt./360
See application file for complete search history.

*Primary Examiner* — Annette Para
(74) *Attorney, Agent, or Firm* — Barbara Campbell; Bethany R. Roahrig; Cochran Freund & Young, LLC

(57) ABSTRACT

A new *Osteospermum* plant particularly distinguished by a compact plant with good branching, flowers composed of ray florets having a purple base and a white and purple stripe towards the tips with white-grey disc florets, and flowers open pale colored and flower color increases in intensity over the next 2 to 3 flowering days, is disclosed.

1 Drawing Sheet

Genus and species: *Osteospermum hybrida.*
Variety denomination: 'SAKOST8340'.

BACKGROUND OF THE NEW PLANT

The present invention comprises a new and distinct variety of *Osteospermum,* botanically known as *Osteospermum hybrida,* and hereinafter referred to by the variety name 'SAKOST8340'. 'SAKOST8340' originated from a hybridization in May-June 2008 in Marslev, Denmark of the proprietary female *Osteospermum* variety '206156' (unpatented) and the commercial male *Osteospermum* variety 'SAKOST8201' (U.S. Publication No. 2012/0278960). The goal of this breeding program was to create a plant having white and purple ray florets and white-grey disc florets.

In May-June 2008, the two *Osteospermum* lines '206156' and 'SAKOST8201' were crossed and seeds were obtained. The seeds were sown and plants were grown in pots for evaluation. In winter 2008-2009, a line was selected.

In February 2009, the line was first vegetatively propagated by cuttings and re-evaluated in an open field and a greenhouse in May 2009. In June 2009 and autumn 2010, the line was selected for further trialing and the stability of the distinct characteristics of this variety was confirmed.

The line was subsequently designated 'SAKOST8340' and was found to reproduce true to type in successive generations of asexual propagation via vegetative cuttings.

SUMMARY

The following are the most outstanding and distinguishing characteristics of this new variety when grown under normal horticultural practices in Salinas, Calif.

1. Compact plant with good branching;
2. Flowers composed of ray florets having a purple base and a white and purple stripe towards the tips with white-grey disc florets; and
3. Flowers open pale colored and flower color increases in intensity over the next 2 to 3 flowering days.

DESCRIPTION OF THE PHOTOGRAPHS

This new *Osteospermum* plant is illustrated by the accompanying photographs which show the plant's overall plant habit including form, foliage, and flowers. The photographs were taken in January 2013 and are of a plant grown seven months from transplant into 6-inch pots from rooted cuttings in Salinas, Calif. under greenhouse conditions. The colors shown are as true as can be reasonably obtained by conventional photographic procedures.

DESCRIPTION OF THE NEW VARIETY

Figure 1:
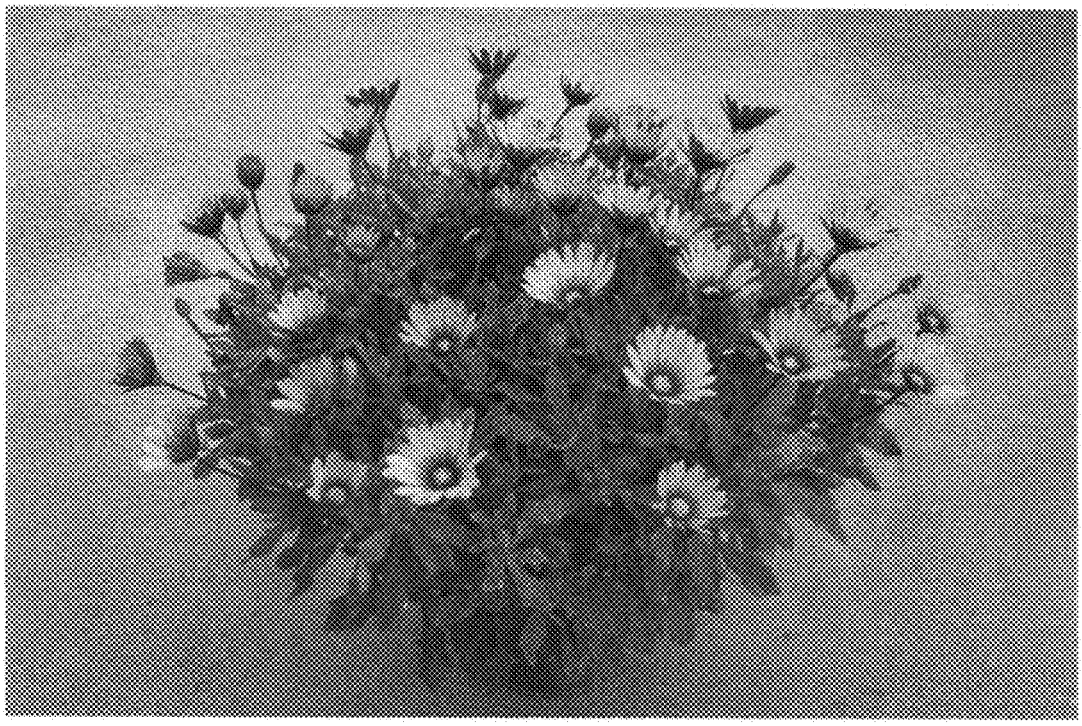
FIG. 1 shows the overall plant habit of the plant grown in a pot.
Figure 2:
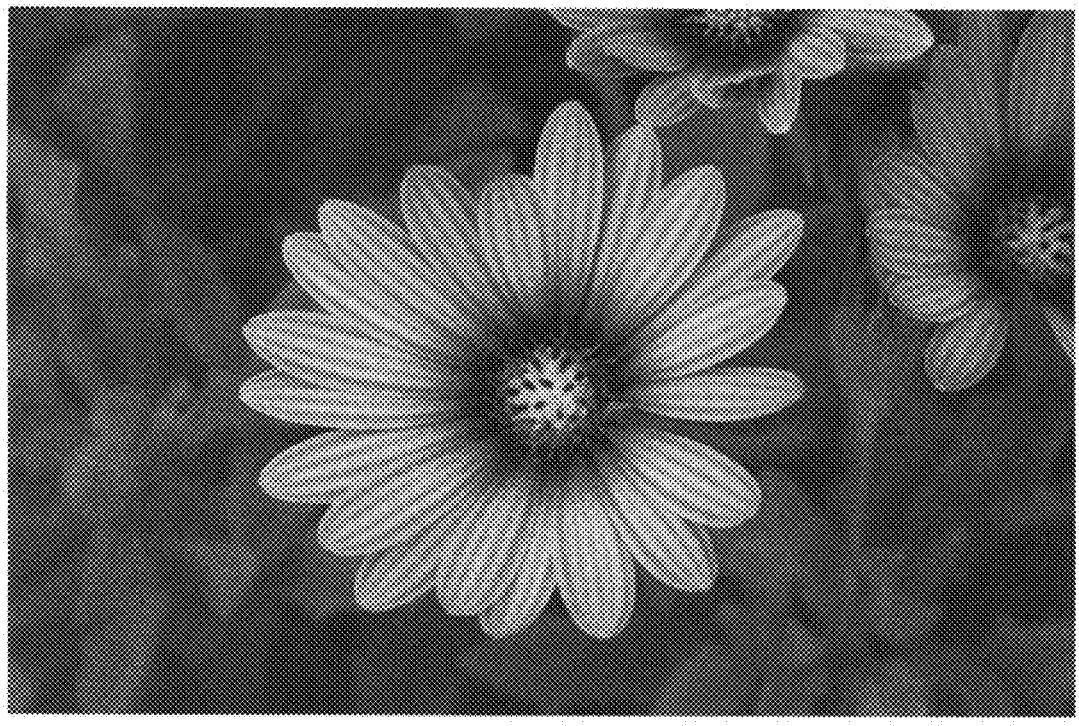
FIG. 2 shows a close-up of the mature inflorescence of the plant.

The following detailed descriptions set forth the distinctive characteristics of 'SAKOST8340'. The data which define these characteristics were collected from asexual reproductions carried out in Salinas, Calif. Data was collected in January 2013 on 20-week-old plants grown approximately seven months from transplant into 6-inch pots under greenhouse conditions in Salinas, Calif. Color references are to The R.H.S. Colour Chart of The Royal Horticultural Society of London (R.H.S.), $4^{th}$ edition. Anatomic labels are from *The Cambridge Illustrated Glossary of Botanical Terms*, by M. Hickey and C. King, Cambridge University.

Classification:
- *Family.*—Compositae.
- *Botanical.*—*Osteospermum hybrida.*
- *Common.*—*Osteospermum, South African Daisy.*
- *Designation.*—'SAKOST8340'.

Parentage:
- *Female parent.*—The proprietary *Osteospermum* variety '206156' (unpatented).
- *Male parent.*—The commercial male *Osteospermum* variety 'SAKOST8201' (U.S. Publication No. (2012/0278960).

Growth:

*Time to produce a rooted cutting.*—Cuttings will colonize a 2.5 cm diameter by 2.5 cm tall greenhouse tray cell with peat-based plant media in approximately four weeks. Cuttings are dipped in a normal dilution (1:9) of DIP 'N GROW, A root inducing solution, in water. The trays are misted hourly during rooting.

*Environmental conditions for plant growth.*—Rooted cuttings are transplanted to pots with a 16 cm diameter, one plant per pot. Peat-based growing media is used. The pots are watered using a 150 ppm to 200 ppm fertilizer solution using 18-8-18 fertilizer. The soil is allowed to dry between watering. During the first few weeks after transplanting, the plants should have evening temperatures around 15° C. to 18° C. for good root growth. When plants reach 7.5 cm to 10 cm in height they are pinched back to 5 to 6 leaves to promote branching. Spring and summer daytime high temperatures in Salinas, Calif. where the data was collected, range from 16° C. to 25° C.

*Time to bloom from propagation.*—Approximately four weeks when rooted vegetative cuttings are transferred to a 16 cm diameter pot. Flowering season is all year in the United States. Vernalization is not required to induce flowering.

Plant description:

*Form.*—Erect, branching.

*Height (from soil line to top of foliage).*—30.0 cm.

*Width.*—55.0 cm.

Branches:

*General.*—1 main, 8 total; circular in cross-section.

*Length (total).*—20.0 cm; approximately 1.0 cm from the soil line to the first node and 2.0 cm between the first and second nodes.

*Diameter.*—0.7 cm.

*Internode length.*—2.0 cm.

*Color.*—RHS 143A (Green).

*Pubescence.*—Absent.

*Appearance.*—Dull.

*Anthocyanin color.*—Absent.

Stems:

*General.*—Multiple, circular in cross-section.

*Length.*—12.0 cm.

*Diameter.*—0.3 cm.

*Internode length.*—1.5 cm.

*Color.*—RHS 143A (Green).

*Pubescence.*—Slight, color is RHS N155A (White), short, hair-like fibers.

*Anthocyanin color.*—Slight, RHS 187A (Greyed-Purple).

Leaves:

*Arrangement.*—Alternate.

*Shape.*—Oblanceolate.

*Apex.*—Acute.

*Base.*—Attenuate.

*Margin.*—Serrate.

*Venation.*—Pinnate.

*Surface appearance (both surfaces).*—Dull.

*Surface pubescence (both surfaces).*—Slight.

*Attachment.*—Decurrant.

*Length.*—6.0 cm.

*Width.*—2.2 cm.

*Thickness.*—Less than 0.1 cm.

*Color.*—Upper surface: Closest to RHS 146A (Yellow-Green). Lower surface: Closest to RHS 146B (Yellow-Green).

*Venation color (both surfaces).*—Closest to RHS 146D (Yellow-Green).

Inflorescence:

*Number per plant.*—40 to 50 in bloom.

*Type.*—Capitulum (head); disc florets are perfect and ray florets are carpellate.

*Flowering habit.*—Determinate.

*Lastingness of inflorescence on the plant.*—3 to 4 days.

*Fragrance.*—Absent.

*Seed production.*—None observed.

*Diameter.*—5.0 cm.

*Depth.*—1.0 cm.

*Petal (ray floret) number.*—17 per inflorescence.

*Disc diameter.*—1.2 cm.

*Disc floret number.*—50 to 60 per inflorescence.

*Peduncle length.*—11.0 cm.

*Peduncle diameter.*—0.2 cm.

*Peduncle color.*—RHS 143A (Green) with RHS 187A (Greyed-Purple) anthocyanin.

*Peduncle texture.*—Dull, slight pubescence; pubescence color is RHS N155A (White).

*Phyllaries.*—Arrangement: 16 per inflorescence, free, arranged symmetrically. Length: 1.0 cm. Width: 0.2 cm. Apex: Acute. Margin: Entire. Shape: Linear; acute. Color (for both upper and lower surfaces): RHS 143C (Green).

Ray florets (ligules):

*Corolla.*—One ray per ray floret; only the outer row of florets are the ray florets.

*Number of ray florets.*—21 per inflorescence.

*Length.*—3.0 cm.

*Width.*—0.7 cm.

*Shape.*—Lanceolate.

*Apex.*—Acute.

*Margin.*—Entire.

*Base.*—Attenuate.

*Color.*—Upper surface: RHS 76C (Purple) with RHS N81A (Purple-Violet) stripes and at the base. Lower surface: Closest to RHS 182B (Greyed-Red) with RHS 187A (Greyed-Purple) stripes.

*Pubescence.*—Glabrous.

Disc florets:

*Color.*—Closest to RHS 97C (Violet-Blue).

*Shape.*—Tubular.

*Apex.*—Acute.

*Texture.*—Dull, pubescent, shiny.

*Size.*—Length: 0.6 cm. Width: 0.1 cm.

*Bud length.*—0.7 cm.

*Bud width.*—0.1 cm.

Reproductive organs:

*Ovary.*—Superior.

*Stigma color.*—RHS 155A (White).

*Pistil form.*—One style with two stigma branches.

*Pistil length.*—0.6 cm.

*Stamens.*—5, fused into a single tube.

*Style color.*—RHS 155A (White).

*Anther color.*—RHS N186A (Greyed-Purple).

*Pollen color.*—RHS 17A (Yellow).

*Filament color.*—RHS 155A (White).

Disease and insect resistance: *Osteospermum* is very disease resistant, however, the plants are susceptible to aphids, thrips, whiteflies, and worms.

COMPARISON WITH PARENTAL LINES AND KNOWN VARIETY

'SAKOST8340' is a distinct variety of *Osteospermum* with flowers composed of ray florets having a purple base and a white and purple stripe towards the tips with white-grey disc florets. 'SAKOST8340' is distinguished from its parents as described in Table 1 (color references are to The Royal Horticultural Society Colour Chart, 4th edition).

TABLE 1

Comparison with Parental Lines

| Characteristic | 'SAKOST8340' | Female Parent '206156' | Male Parent '207102' |
|---|---|---|---|
| Ray floret color | Upper surface is RHS 76C (Purple) with RHS N81A (Purple-Violet) stripes and at the base; Lower surface is closest to RHS 182B (Greyed-Red) with RHS 187A | White | Upper surface is RHS 155D (White) with RHS 72B (Red-purple) stripes and at base; Lower surface is RHS 155D (White) with stripes of RHS 77A, B and C (Red-purple) |

'SAKOST8340' is a distinct variety of *Osteospermum* with flowers composed of ray florets having a purple base and a white and purple stripe towards the tips with white-grey disc florets. 'SAKOST8340' can be compared to 'SAKOST8181' (U.S. Plant Pat. No. 23,502). Differences between the two varieties are described in Table 2 (color references are to The Royal Horticultural Society Colour Chart, 4th edition).

TABLE 2

Comparison with Similar Variety

| Characteristic | 'SAKOST8340' | 'SAKOST8181' |
|---|---|---|
| Ray floret color | RHS 18C (Yellow-Orange) with RHS 75A (Purple) stripes and streaks; RHS 75A (Purple) at the base and RHS 10A (Yellow) at the tip | Upper surface is RHS 77A (Purple) and lower surface is RHS 77B (Purple) |

I claim:

1. A new and distinct variety of *Osteospermum* plant as shown and described herein.

* * * * *